(12) United States Patent
Kai et al.

(10) Patent No.: US 6,514,728 B1
(45) Date of Patent: Feb. 4, 2003

(54) PROCESS FOR PREPARATION OF CYTOKINES USING SENDAI VIRUS EXPRESSION SYSTEM

(75) Inventors: Chieko Kai, Tokyo (JP); Atsushi Kato, Tokyo (JP)

(73) Assignee: Nippon Biocaptal Limited, Tokyo (JP)

( * ) Notice: Subject to any disclaimer, the term of this patent is extended or adjusted under 35 U.S.C. 154(b) by 0 days.

(21) Appl. No.: 09/436,504

(22) Filed: Nov. 9, 1999

(30) Foreign Application Priority Data

Nov. 9, 1998 (JP) .......................................... 10-317321

(51) Int. Cl.⁷ .............................. C12N 7/00; C12N 7/02; C12N 15/63; C12N 15/85
(52) U.S. Cl. ................... 435/69.5; 435/235.1; 435/239; 435/325; 435/349; 435/455; 435/69.1
(58) Field of Search ................................. 424/520, 581; 435/69.1, 69.5, 70.3, 235.1, 239, 455, 349, 325; 536/23.1, 23.52

(56) References Cited

U.S. PATENT DOCUMENTS

| | | | | |
|---|---|---|---|---|
| 3,560,611 A | * | 2/1971 | Chany et al. | 428/85 |
| 4,276,282 A | * | 6/1981 | Sugimoto et al. | 424/85 |
| 4,285,929 A | * | 8/1981 | Sugimoto et al. | 424/85 |
| 5,162,215 A | * | 11/1992 | Bosselman et al. | 435/172.3 |
| 5,518,899 A | * | 5/1996 | Kurimoto et al. | 435/70.5 |
| 5,641,656 A | * | 6/1997 | Sekellick et al. | 435/69.51 |

FOREIGN PATENT DOCUMENTS

| | | |
|---|---|---|
| EP | 0863202 A | 9/1998 |
| EP | 0864645 A | 9/1998 |
| WO | 97/16539 | 5/1997 |

OTHER PUBLICATIONS

Sakaguchi et al. Expression of HN, F, NP, and M proteins of Sendai virus by recombinant vaccinia viruses and their contribution to protective immunity against Sendai virus infections in mice. J Gen Virology 74: 479–484, 1993.*
DeVos, K., et al, "Cloning and Expression of the Canine Interferon–Gamma Gene", Journal of Interferon Research 1992, vol. 12, No. 2, 1992, pp. 95–102.
Hasan, Mohammad K., et al, "Creation of an Infectious Recombinant Sendai Virus Expressing the Firefly Luciferase Gene from the 3' Proximal First Locus", Journal of General Virology, Nov. 1997, vol. 78, No. 11, pp. 2813–2820.
Moriya, Chikaya, et al, "Large Quantity Production with Extreme Convenience of Human SDF–1x and SDF–1β by a Sendai Virus Vector", FEBS Letters, Mar. 20, 1998, vol. 425, No. 1, pp. 105–111.
Zucker, K. et al, "Cloning of the CDNA for Canine Interferon–Gamma", Journal of Interferon Research 1992, vol. 12, No. 3, 1992, pp. 191–194.
Database WPI, Section Ch, Week 199746, Derwent Publications, Ltd., London, GB; Class B04 AN 1997–497324.

* cited by examiner

*Primary Examiner*—Gary L. Kunz
*Assistant Examiner*—Bridget E. Bunner
(74) *Attorney, Agent, or Firm*—Burns, Doane, Swecker & Mathis, LLP

(57) ABSTRACT

The present invention provides a process for preparing a cytokine inexpensively in large amounts by expressing the cytokine in a hen's egg using Sendai virus vector. The cytokine obtained by the present process is expected to be useful as medication because it has sugar chains very similar to those of mammals.

10 Claims, 3 Drawing Sheets

MHC classII induction on MDCK cells by canine IFNγ

Sendai virus-Allantoic fluid

1: mock
2: control Sendai virus
3: cIFNγ-SeV

MHC classII induction on MDCK cells by canine IFNγ

Baculo virus-Sf9 cell

4: mock
5: control Baculo virus
6: cIFNγ-Baculo

```
                       SEQUENCE LISTING

<160> NUMBER OF SEQ ID NOS:   6

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:cytokine
      using sendai virus

<400> SEQUENCE: 1
aagcggccgc ttcaccacca tgaattatac aagct                         35

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:cytokine
      using sendai virus

<400> SEQUENCE: 2
ctcgatttct ttaaaaaaca tggcc                                    25

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:cytokine
      using sendai virus

<400> SEQUENCE: 3
atcgagaacc taaaggaata ttttaatg                                 28

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence:cytokine
      using sendai virus

<400> SEQUENCE: 4
ttgcggccgc gatgaacttt caccctaagt ttttcttact accattattt cgatgctc    58
```

-continued

```
<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:cytokine
      using sendai virus

<400> SEQUENCE: 5
ctttgctttg ctgccaaag                                              19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:cytokine
      using sendai virus

<400> SEQUENCE: 6
tttcgctcct cctagagc                                               18
```

PROCESS FOR PREPARATION OF CYTOKINES USING SENDAI VIRUS EXPRESSION SYSTEM

TECHNICAL FIELD

The present invention relates to a process for the preparation of a cytokine by genetic recombination technology. More particularly, the present invention relates to a process for preparing a cytokine useful as a medicine inexpensively in large amounts by expressing the cytokine in eggs using Sendai virus vector.

BACKGROUND OF THE INVENTION

Cytokines such as interferons (IFN), interleukins, colony-stimulating factors (CSF) and tumor necrosis factors (TNF) are proteinous physiologically active biogenic substances which control cellular responses such as cell replication, differentiation, maintenance of existence, cell death, or expressions of functions, regulate immune system and inflammation reaction, and maintain homeostasis in cells or tissues. A cytokine network is formed because a single cytokine has many activities (pleiotropy), some cytokines have redundant activities (redundancy), and many cytokines have interactions in a single cell.

The most commonly known interferons are interferon $\alpha$, $\beta$ and $\gamma$, which have antivirus activities, inhibitory activities on cell proliferation, and regulatory activities on immunity, etc.

Interleukins are a group of biologically active substances which are produced by immunocompetent cells such as lymphocytes, monocytes, or macrophages. At present interleukins 1–18 have been elucidated. Colony-stimulating factors include a granulocyte colony-stimulating factor (G-CSF) having an activity for forming neutrophil colonies, a-macrophage colony-stimulating factor (M-CSF) having an activity for forming a macrophage colony, and a granulocyte macrophage colony-stimulating factor (GM-CSF) having an activity for forming a granulocyte/macrophage mixed colony. Other cytokines include a tumor necrosis factor (TNF), a transforming growth factor (TGF-$\beta$) super family including TGF-$\beta$ as a representative, growth factors such as an epidermal growth factor (EGF) or a platelet-derived growth factor (PDGF), and hematopoietic factors such as erythropoietin or thrombopoietin.

Some of the cytokines described above have been commercially manufactured by genetic recombination technology or are in the course of development since they are useful as agents for treatment of various infectious diseases, tumors, thrombocytopenia, neuropenia, aplastic anemia, etc.

Generally, when medications comprising proteins or peptides are prepared from organs or blood, there are problems of shortage and high cost of materials, risk of infection, etc. In order to solve these problems, methods for preparing proteins or peptides as medications by utilizing genetic engineering have been developed. As mass expression systems of proteins for medical use, there have been expression systems using a procaryote such as $E$. $coli$ as a host, those using yeast which is eucaryotic and unicellular cell as a host, those using a baculovirus expression system and employing insect cells as a host, those using mammalian cells such as Chinese hamster ovary cells (CHO cells) as a host, etc. Also, recently it has become possible to produce transgenic animals which are animal individuals integrated by foreign genes, and methods for preparing useful proteins by using these animals have been developed. For example, a method in which a characteristic is expressed specifically in mammary gland cells such as those of a cow, a sheep, or a goat, a useful protein is secreted into milk, and the protein of interest is recovered is anticipated as a mass expression system for preparing useful proteins. At present, such a method is being developed as an inexpensive method for preparing blood preparations such as human serum albumin, and it has been attempted to secrete the thrombolytic drug, t-PA, into goat milk.

As to production of cytokines using genetic engineering, interferon-$\alpha$, interferon-$\beta$, interferon-$\gamma$, interleukin-2, etc. have been produced or proposed to be produced in $E$. $coli$ systems, G-CSF and interleukin-11 have been produced or proposed to be produced in CHO cell systems, and GM-CSF has been produced or proposed to be produced in yeast systems.

However, the above-described prior art expression systems for useful proteins have various problems, and especially when the protein of interest has sugar chains, there is a problem of whether sugar chains can be bound to the expressed protein in a host of an expression system. In $E$. $coli$ systems, mass culturing can be carried out and the growth rate is high, but sugar chains are not bound to expressed proteins. Also, in $E$. $coli$, the proteins which are produced are usually accumulated within the cells, and therefore, isolation and purification including isolation of cells from the culture medium are expensive. In baculovirus expression systems using insect cells, sugar chains are bound, but are bound in a different way from in mammals. Expression systems using mammalian cells as hosts are not practical since the yield is extremely low, the cost is high especially when CHO cells which require expensive fetal bovine serum are used, and there is a risk of contamination of retrovirus in the cells.

Methods using transgenic animals require much labor and money when producing transgenic animals for the first time, and the amount of expression is still inadequate.

In order to put a method for preparation of a useful protein by recombinant DNA technology to practical use, it is important whether the produced protein is naturally occurring, what are the effects and side effects of the protein as a medication, and whether the protein can be expressed in large amounts and effectively. The ease and cost of isolation and purification, the maintenance of protein activity during a purification process, and the ease of formulation of drugs are also important.

As mentioned above, it is difficult to produce cytokines having sugar chains in a way similar to mammals in the form of naturally occurring proteins in large amounts and inexpensively by prior art expression systems for proteins.

SUMMARY OF THE INVENTION

It is an object of the present invention to provide a process for producing a naturally occurring cytokine in large amounts and inexpensively.

As a result of investigation to solve the problems of the prior art expression systems for proteins described above, the present inventors found that proteins having sugar chains close to those of mammals can be produced in large amounts and inexpensively by using Sendai virus vector and expressing the proteins in hen's eggs, and also found that in the present system the proteins are released into the chorioallantoic fluid of hen's eggs in large amounts, so isolation and purification can be easily conducted, thereby stablishing a mass production system for cytokines.

In one aspect, the present invention provides a process for preparing a cytokine, comprising infecting an egg with recombinant Sendai virus containing a gene coding the cytokine and recovering the expressed cytokine.

The recombinant Sendai virus can be produced in a cell by insertion of a gene coding the cytokine into a Sendai virus genome to produce a recombinant Sendai virus genome containing said cytokine gene and introduction of the resulting construct into the cell. The cell to be used for production of the recombinant Sendai virus may be a cell that expresses nucleocapsid protein (NP), phosphoprotein (P/C) and large protein (L) of the Sendai virus.

The expressed cytokine may be recovered from the chorioallantoic fluid of the infected egg.

The cytokine obtained in accordance with the present process has sugar chains, or the expressed cytokine is glycosylated.

The present process can be preferably applied to the process for preparation of interleukins.

DETAILED DESCRIPTION OF THE PREFERRED EMBODIMENTS

Figure 1:
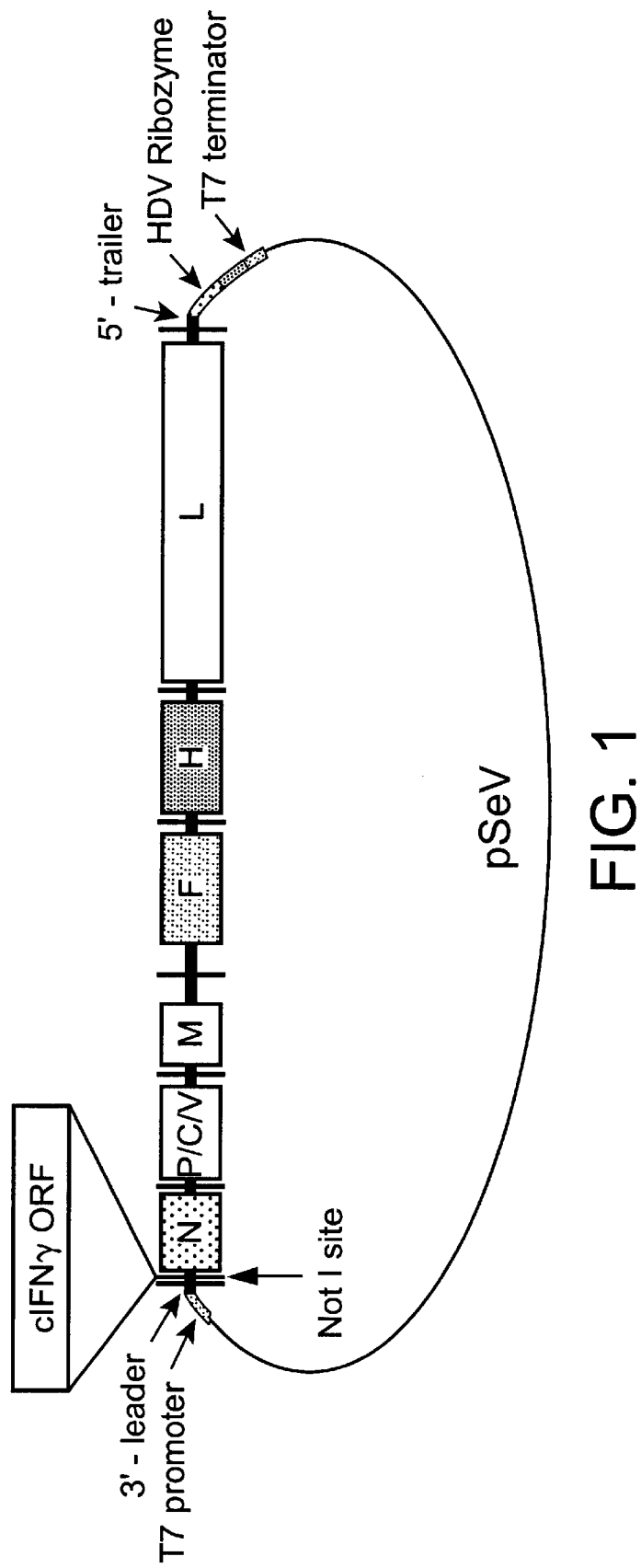
FIG. 1 is a view showing the constitution of recombinant Sendai virus vector inserted by canine IFN-γ gene.

In a preferred embodiment, a cytokine may be expressed by inserting a gene coding a cytokine such as interferons of interleukins into a Sendai virus vector genome, introducing the resulting construct into a suitable cultured cell which is capable of expressing early transcription and replication enzymes by a suitable technique such as transfection to reconstruct Sendai virus, thereby producing recombinant Sendai virus, and infecting hen's eggs with this virus to express the cytokine in the eggs as a host. The produced cytokine may be recovered after being released into chorioallantoic fluid of the eggs.

Sendai virus used as an expression vector in the present invention is classified as parainfluenza 1 virus of the Paramyxovirus genus of the Paramyxoviridae family, and is named HVJ (Hemagglutinating virus of Japan), but is often called SeV.

According to classification by genomic nucleic acid, Sendai virus belongs to a group of minus single-stranded RNA virus of minus strand RNA virus of RNA virus. Among the RNA viruses having RNA as a genome, a genome of plus strand RNA virus has infectivity by itself, but a genome of minus strand RNA virus has no infectivity. That is to say, when plus strand RNA genome is introduced into a cell, this also functions as mRNA, and therefore the proteins necessary for replication and particle formation can be produced depending on the translational function of a host cell to form progeny viruses.

However, the genomes of minus strand RNA viruses to which Sendai virus belongs cannot function as MRNA, and therefore genetic information cannot be expressed with minus strand RNA genome is introduced into a cell. Minus strand RNA virus has RNA-dependent RNA polymerase in the virus particle, and soon after infection genomic RNA of minus strand RNA virus is transcribed to plus strand RNA, i.e., mRNA. Also, Sendai viral RNA transcribed artificially in vitro does not produce virus particles, whether it is plus strand or minus strand, when it is introduced alone into a cell.

In order to use a virus as a vector, it is necessary to reconstruct virus particles from virus genomes having foreign genes integrated by gene manipulation. Methods for reconstructing Sendai viruses are disclosed particularly in International Publication No. WO97-16539. The establishment of the reconstruction technique for Sendai viruses has made it possible to reconstruct recombinant Sendai viruses from Sendai virus genomes inserted by foreign genes and use Sendai virus as an expression vector.

The following methods are exemplified as methods for reconstructing Sendai virus.

(1) Recombinant cDNA coding recombinant Sendai virus vector genome constructed by genetic engineering is transcribed in vitro to produce recombinant Sendai virus genomic RNA, and this RNA is incorporated into a host which is able to express NP protein, P/C protein, and L protein of Sendai virus (each protein may be a protein having an equivalent activity) concurrently to obtain recombinant Sendai virus vector.

(2) (i) Recombinant cDNA coding recombinant Sendai virus vector genome constructed by genetic engineering and (ii) a unit capable of transcribing this DNA as a template to form RNA are incorporated into a host which is able to express NP protein, P/C protein, and L protein of Sendai virus (each protein may be a protein having an equivalent activity) concurrently to obtain recombinant Sendai virus vector (in this case, for example, (i) is linked downstream of a particular promoter, and (ii) is DNA capable of expressing DNA-dependent RNA polymerase which acts on this particular promoter).

Examples of hosts which are able to express NP protein, P/C protein, and L protein of Sendai virus concurrently includes cells which are able to express all early transcription and replication enzymes, such as 293 cell-derived cells containing NP, P/C, and L genes among Sendai virus genes in the chromosome, which cells are expressing NP protein, P/C protein and L protein. Alternatively, when recombinant Sendai virus genomic RNA or cDNA is incorporated into a cell, plasmids capable of expressing NP, P/C, and L protein may be cotransfected.

Sendai virus used in the present invention to be inserted by a cytokine gene may be a strain belonging to parainfluenza 1 virus, such as Sendai virus Z strain or Sendai virus Fushimi strain. Also, incomplete particles such as DI particles, synthesized oligonucleotides, etc. may be used as a part of starting materials.

Examples of cytokine genes which are inserted into Sendai virus vectors used in the present invention include genes encoding various interferons (interferon α, β and γ), various interleukins (interleukin 1–18), colony-stimulating factors (G-CSF, M-CSF, GM-CSF, etc.), tumor necrosis factors (TNF-α, etc.), hematopoietic factors (erythropoietin, thrombopoietin, etc.), TGF-β super family (TGF-β, beta-glycan, activin, inhibin, BMP family, follistatin etc.), growth factors (EGF, TGF-α, HB-EGF, amphireglin, PDGF, FGF, IGF, HGF, VEGF, NGF, etc.) And other genes coding TNF/LT, Fas, etc.

The preparation and cloning of these genes may be conducted by any conventional method, such as by selecting the gene using binding with a gene fragment or specific antibody or protein as an index from a cDNA library prepared from RNA in tissues or cells capable of expressing the gene. Preferably, this may be conducted by PCR (polymerase chain reaction) technique using primers designed from the reported sequence of the gene.

Insertion of a cytokine gene into a Sendai virus vector genome may be carried out in a conventional manner, and it is known that when the site of the insertion is nearer to the NP gene, the inserted gene is expressed more.

Sendai virus vector genome having a cytokine gene inserted is reconstructed into Sendai virus in a suitable cultured cell as explained above to obtain a recombinant Sendai virus.

In accordance with the present invention, hen's eggs are used as a host for expressing a protein. Eggs are infected with the recombinant Sendai virus containing a cytokine gene as obtained above, and the expressed cytokine is recovered from chorioallantoic fluid of the eggs. Cytokine may be recovered, for example, by concentration using ultrafiltration dependent on molecular weight after the removal of Sendai virus by centrifugation, and may be purified most conveniently by the affinity column technique using an antibody against the cytokine. When the affinity column technique cannot be used, the purification may be carried out by various types of chromatography such as ion exchange, gel filtration, or reverse phase chromatography.

The cytokine produced in eggs has high biological activity and stability and is supposed to have little side effects, since it has sugar chains which are bound in a similar form to those of mammals, unlike the prior art cytokines produced in an E. coli host or in a host of insect cells using baculovirus as a vector. Furthermore, Sendai virus itself is not pathogenic to human being and animals except mice and therefore is safe, while Sendai virus can be removed in a purification process of an expressed cytokine.

In accordance with the present invention, a cytokine can be produced effectively in large amounts, since Sendai viruses containing a cytokine gene grow well in eggs, and an expressed cytokine is released in large amounts into choriballantoic fluid. Additionally, eggs are inexpensive and easily available stock food, and the recovery and purification of a cytokine from chicken eggs is relatively simple and easy. Therefore, the method of the present invention is very useful for practical mass production of a cytokine.

The following examples are given to further illustrate the present invention, but it should be understood that the present invention is not limited to the specific details set forth in the examples.

EXAMPLE 1

This example illustrates the production of canine interferon-γ (IFN-γ) using a Sendai virus vector.

IFN-γ has antivirus and antitumor activities, and plays an important role as a mediator of the cytokine network. IFN-γ promotes THI type immune response, and predominantly induction of class I and class II of major histocompatibility complex (MHC), induction of intercellular adhesion molecule-1(ICAM-1), activation of 2', 5'-oligoadenylate synthetase-RNase L pathway, and induction of apoptosis by induction of Fas and Fas ligand are raised. Therefore, it is applied to treatment of various infectious diseases and tumors. Also, it is expected to be useful as a cytokine adjuvant in vaccination. However, experiments in humans are difficult to conduct, and therefore it is difficult to determine using human models how efficacious treatment of these various infectious diseases and tumors using IFN-γ would be. As a result of this difficulty, an animal model has to be used. A particular good animal model is a dog, which has a prolonged life span like humans. The dogs were subjected to actual clinical treatment and vaccination, and canine IFN-γ was expressed using a Sendai virus expression system as a mass expression system.

(i) Preparation of Sendai Virus Vector Containing Canine IFN-γ Gene

Canine IFN-γ gene was cloned by amplifying open reading frame coding canine IFN-γ by PCR technique using the following primers 1–4. The nucleotide sequence of canine IFN-γ gene is described in K.Devos et al., Journal of Interferon Research Vol.12, p.95–102 (1992) and K.Zucker et al., Journal of Interferon Research Vol.12, p.191–194 (1992).

Primer 1: AAGCGGCCGCTTCACCACCATGAAT-TATACAAGCT (SEQ ID No:1) Not1 site

Primer 2: CTCGATTTCTTTAAAAAACATGGCC (SEQ ID NO:2)

Primer 3: ATCGAGAACCTAAAGGAATATTTTAATG (SEQ No:3)

Primer 4: TTGCGGCCGCGATGAACTTTCAC-CCTAAGTTTTTCTTACTACCATTATTTCGATGCTC Not1 site transcription transcription initiation signal termination signal (SEQ ID No:4)

In order to insert cDNA clone of cloned canine IFN-γ into Sendai virus vector, the primer having Not1 site at 5'terminus (primer 1) and the primer having Not1 site at 5'terminus and having the transcription initiation signal and the transcription termination signal which are necessary for transcription in Sendai virus (primer 4) were designed. Since there is a nucleotide sequence in canine IFN-γ which is similar to the transcription termination signal of Sendai virus, and since if this sequence is integrated into Sendai virus, there will be a risk of terminating transcription at the site of the signal so as not to express canine IFN-γ of interest, the sequence was modified without the change of the amino acids.

First, PCR was carried out in the combination of primer 1 and primer 2 and in the combination of primer 3 and primer 4, and each of the amplified fragments was extracted from the gel used for electrophoresis. Then, PCR was carried out using a mixture of the amplified fragments as a template and using primer 1 and primer 4, and TA cloning was conducted. The sequence was confirmed by the dideoxy method.

A part of the canine IFN-γ was changed by this PCR as follows:

nucleotide sequence ATAGAA→ATCGAG amino acid Ile/Glu→Ile/Glu

From the plasmid containing the modified canine IFN-γ gene fragment, canine IFN-γ gene was excised with restriction enzyme Not1, the primer having the Not1 restriction site, and inserted at the Not1 restriction site of Sendai virus vector (see FIG. 1). This plasmid was purified by cesium chloride density-gradient ultracentrifugation and was used for transfection as explained below.

(2) Reconstruction of Recombinant Sendai Virus and Recovery Thereof from Eggs

The plasmid containing canine IFN-γ gene fragment obtained above was cotransfected along with the following plasmids capable of expressing three constitutive proteins of Sendai virus into LLCMK2 cells infected with vaccinia virus, and recombinant Sendai virus particles were produced.

pGEM-N: gene coding nucleocapsid protein pGEM-P: gene coding phosphorylating protein pGEM-L: gene coding large RNA polymerase Vaccinia virus (vTF7-3) has T7 RNA polymerase gene for expressing the above three plasmids within the cell by genetic recombination.

Reconstruction and recovery of recombinant Sendai virus from eggs were carried out as follows:

Vaccinia viruses (vTF7-3) were absorbed into $2.0\times10^6$ cells of LLCMK2 cell prepared in a petri dish as a moi (multiplicity of infection) of 2 plaque forming units (PFU) for 1 hour, and the cells were washed twice with PBS. DOTAP (Boelinger Manhaim Corp.) solution containing 10 µg of the plasmid containing the canine IFN-γ gene fragment (PIFN-γ-SeV), 4 µg of pGEM-4, 2 µg of pGEM-P, and 4 µg of pGEM-L was added dropwise to the cells. The cells were cultured for 40 hours in the presence of 40 µg/ml of citocine arabinoside and 100 µg/ml of rifampicin and then the cells were recovered, and after three freezings and thawings the supernatant was recovered.

Recombinant Sendai viruses were supposed to be produced and contained in the supernatant, and therefore about 1000 fold-diluted supernatant was inoculated into chorioallantoic cavity of 10-day old chicken embryonic eggs, and chorioallantoic fluid was recovered after three days. The presence of 1024–2048 HAV (hemaglutinin unit) of the viruses was confirmed by HA assay (hemaglutinin assay). Furthermore, subculture was conducted in chicken embryonic eggs where vaccinia viruses cannot grow in order to remove contaminate vaccinia viruses, even if little. The obtained recombinant Sendai viruses were diluted to 0.1–1 HAU, and the diluted viruses were inoculated again into chorioallantoic cavity of 10-day old chicken embryonic eggs and the recovery was conducted in the same manner.

The recovered Sendai virus was confirmed by the RT-RCR method to be recombinant Sendai virus containing a canine IFN-γ gene as follows. Total RNA was extracted from the chorioallantoic fluid of infected chicken embryonic eggs with a commercially available RNA extraction kit, RT-PCR was carried our using the following primers, and the presence of the recombinant Sendai virus was confirmed.

primer 5: CTTTGCTTTGCTGCCAAAG (SEQ ID No:5)

primer 6: TTTCGCTCCTCCTAGAGC (SEQ ID No:6)

Next, the expression of canine IFN-γ was confirmed and bioassay was carried out. The sample described below is the sample wherein Sendai viruses were removed by ultracentrifugation and ultrafiltration from the chorioallantoic fluid obtained above.

(3) Confirmation of the Expression of Canine IFN-γ in Chicken Eggs

The expression of canine IFN-γ protein in the chorioallantoic fluid was confirmed by western blotting assay using antiserum obtained by immunizing a rabbit with canine IFN-γ expressed in E. coli as follows.

Figure 2:
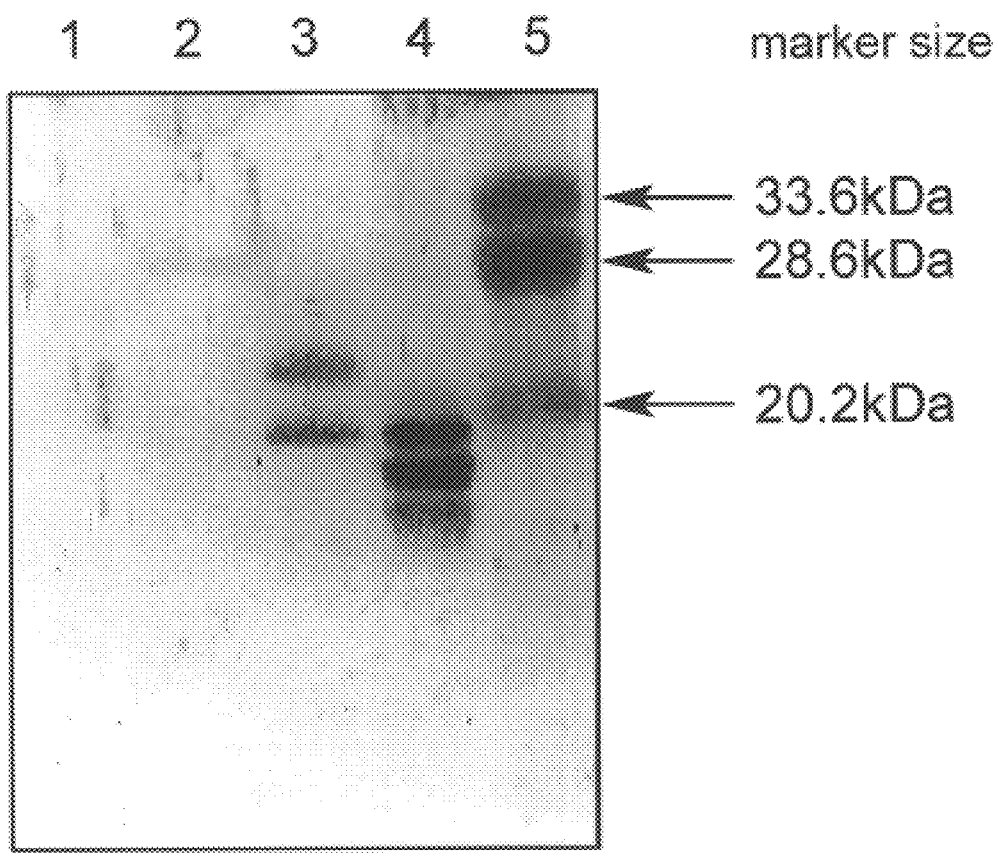
FIG. 2 is a view showing the expression of canine IFN-γ by western blotting analysis using rabbit antiserum against canine IFN-γ expressed in *E. coli*. In lane 3, the bands of 25 and 20 kDa represent the presence of IFN-γ expressed using Sendai virus. In lane 4, the bands of 20, 19 and 17 kDa represent the presence of IFN-γ expressed using baculovirus.

The chorioallantoic fluid infected with recombinant canine IFN-γ-Sendai virus, the chorioallantoic fluid infected with wild Sendai virus, and the chorioallantoic fluid of noninfected chicken embryonic eggs as a complete negative control were each subjected to ethanol precipitation and each precipitate was dissolved into a sample buffer. Also, recombinant canine IFN-γ expressed using baculovirus expression system was dissolved in a sample buffer as a positive control of canine IFN-γ. All samples were subjected to electrophoresis in polyacrylamide gel, and each of the resulting proteins was transferred to a nitrocellulose membrane by s semidry blotting apparatus and was blocked with PBST containing 5% skim milk. The primary antibody reaction was carried out using anti-canine IFN-γ rabbit antiserum diluted 10 fold with PBST containing 3% skim milk, and secondary antibody reaction was carried out using peroxidase-labelled anti IgG rabbit antibody diluted 1000 fold with the same, and then the canine IFN-γ specific band was visualized with diaminobenzidine. This confirmed that the canine IFN-γ protein was expressed in the chorioallantoic fluid infected with canine IFN-γ recombinant Sendai virus. (See FIG. 2)

(4) Bioassay

Bioassay was carried out as follows.

A72 cells were placed at a concentration of $3\times10^{4}$ cells/well on a 96 well plate, and on the next day each 100 µl/ml of serial 2-fold dilutions of the sample were added dropwise to the cells after the supernatant was removed.

After 24 hours, the cells were infected with $100\text{TCID}_{50}$ of Vesicular Somatitis virus (VSV). On the next day, the cells were fixed with formalin dyed with crystal violet, washed, and the dye was eluted and the absorbance was measured. One laboratory unit (1LV) is defined as a concentration where cytopathic effect with VSV is inhibited by 50%. The results are as follows:

Measurement of Titer by Inhibition of Growth of VSV on A72 Cells chorioallantoic fluid infected with recombinant canine IFN-γ-SeV 160 LU/ml chorioallantoic fluid infected with wild SeV <10 LU/ml control chorioallantoic fluid <10 LU/ml This bioassay utilizes the fact that an interferon has antiviral activity to enable determination of the activity of the interferon. Among methods used often for measurement of virus titer, there is a method for measuring it as a degree of cytopathic effect (CPE) which occurs when a virus infects a cell. An interferon has an inhibitory effect on virus growth. When the virus is pretreated with the interferon, the growth of the virus is inhibited, so, the degree of CPE is decreased depending on the interferon activity. One LV is defined as IFN titer of the dilution which inhibits CPE by 50% when the cells pretreated with the sample dilution are infected with the viruses in an amount having 100% CPE.

(5) Purification of canine IFN-γ

The choriballantoic fluid containing canine IFN-γ obtained in (2) was subjected to centrifugation and then ultrafiltration to remove Sendai viruses from the fluid.

If further purification is desired, the following technique is available.

To the resulting fluid, 10 mg/ml of controlled pore glass (PG 350-20, Sigma, USA) is added and rotated at a temperature of 4° C. for 20 hours to absorb canine IFN-γ. After centrifugation, the supernatant is removed and washing with PBS is conducted 4 times. To this, PBS containing 1.4 M NaCl and 50% ethylene glycol is added at a rate of 25 ml/10 g of controlled pore glass Further centrifugation is carried out at 4° C. for 20 hours to release canine IFN-γ, and after centrifugation of supernatant, canine IFN-γ is recovered. The supernatant is dialyzed with Buffer 1 (20 mM Tris.C1, 1 mM DTT, 5% ethylene glycol, 15% glycerol) and added to ion exchange chromatography equilibrated with the solution. The elution is carried out using Buffer 2 (0.5M NaCl is added to Buffer 1) with a linear concentration gradient. The obtained purified canine IFN-γ is further purified by gel filtration chromatography using Hiload 16/60 SUPERDEX 75 and dissolved in a suitable solution. The presence of canine IFN-γ in each step is confirmed by western blotting or bioassay.

(6) Assay for Induction of MHC Class II Molecule Expression by IFN-γ

Figure 3A:
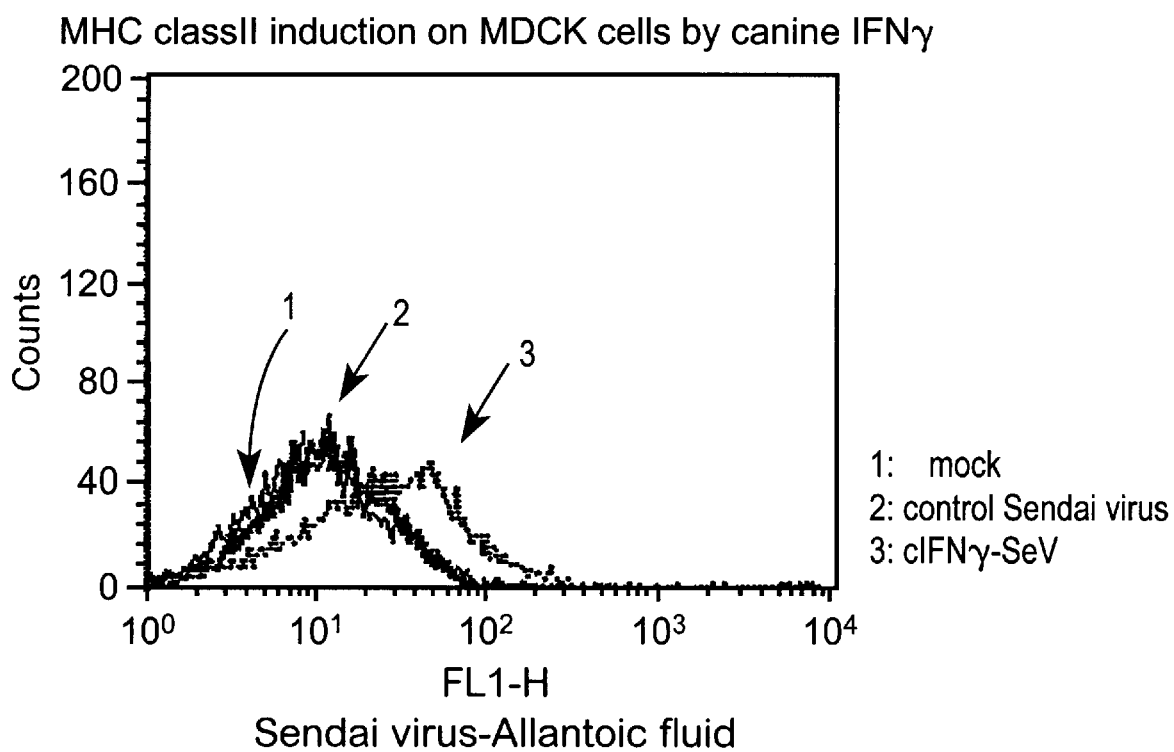
FIGS. 3(*a*) and (*b*) are graphs showing the inductin of MHC class II molecule expression by IFN-γ.
Figure 3B:
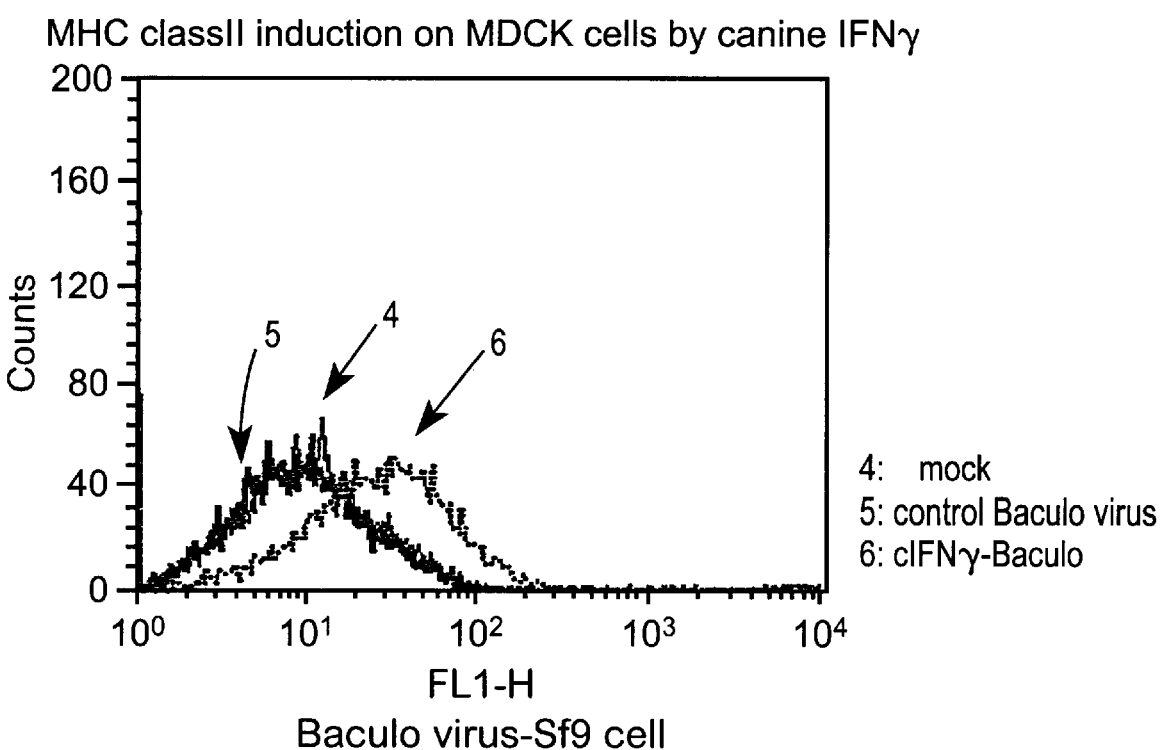

The recombinant IFN-γ expressed in chorioallantoic fluid by Sendai virus was added to a culture medium of MCCK cells of a canine kidney-derived cell strain, and incubation was carried out for 17 hours. Then, the cells were washed with sorter buffer, incubated along with anti-canine MHC class II monochronal antibody for 30 minutes, washed again with sorter buffer, and incubated along with FITC-labeled anti-mouse IgG antibody for 30 minutes. The cells were again washed with sorter buffer and were analyzed by FAC Scan (See FIGS. 3(a) and 3(b)). As a result, it is apparent that IFN-γ expressed using Sendai virus can induce MHC class II molecule expression on the cells, like IFN-γ expressed using baculovirus.

As explained above, according to the present invention, cytokines can be expressed effectively in large amounts in chicken eggs by using Sendai virus vector expression system which is confirmed to be safe, and the purification of the expressed cytokines is easy. The cytokines obtained are expected to be useful for medications because they have sugar chains very similar to those of mammals, unlike the prior art expression system. Therefore, the present invention contributes greatly to putting the system for producing cytokines as useful medications in large amounts inexpensively into practical use.

What is claimed is:

1. A process for preparing a cytokine, comprising infecting a chicken egg with a recombinant Sendai virus containing a gene encoding the cytokine and recovering the expressed cytokine.

2. The process according to claim 1, wherein the recombinant Sendai virus has been produced in a cell by insertion of a gene coding said cytokine into a Sendai virus genome to produce a recombinant Sendai virus genome containing said cytokine gene and introduction of the resulting construct into the cell.

3. The process according to claim 2, wherein the cell to be used for production of said recombinant Sendai virus is a cell that expresses the nucleocapsid protein (NP), phosphoprotein (P/C) and large protein (L) of said Sendai virus.

4. The process according to claim 1, wherein the cytokine is an interferon.

5. The process according to claim 1, wherein said cytokine is recovered from the chorioallantoic fluid of said infected egg.

6. The process according to claim 1, wherein said expressed cytokine is glycosylated.

7. A chicken egg that has been infected with a recombinant Sendai virus that contains a gene encoding a cytokine that results in the production of said cytokine.

8. The egg of claim 7 wherein said cytokine is interferon.

9. The egg of claim 7 wherein said cytokine is gamma interferon.

10. A chorioallantoic fluid composition containing a cytokine isolated from the egg of claim 7.

* * * * *

UNITED STATES PATENT AND TRADEMARK OFFICE
CERTIFICATE OF CORRECTION

PATENT NO. : 6,514,728 B1
DATED : February 4, 2003
INVENTOR(S) : Chieko Kai et al.

It is certified that error appears in the above-identified patent and that said Letters Patent is hereby corrected as shown below:

<u>Title page,</u>
Item [73], is deleted in its entirety, and the following new information is inserted:
-- [73]   Assignee:    Nippon Biologicals, Inc., Tokyo (JP)
                      The University of Tokyo, Tokyo (JP) --

Signed and Sealed this

Ninth Day of September, 2003

JAMES E. ROGAN
*Director of the United States Patent and Trademark Office*